United States Patent
Nakaie

(10) Patent No.: US 10,177,315 B2
(45) Date of Patent: Jan. 8, 2019

(54) ARYLSULFONIC ACID COMPOUND, USE THEREOF, AND METHOD FOR PRODUCING ARYLSULFONIC ACID COMPOUND

(71) Applicant: NISSAN CHEMICAL INDUSTRIES, LTD., Tokyo (JP)

(72) Inventor: Naoki Nakaie, Funabashi (JP)

(73) Assignee: NISSAN CHEMICAL INDUSTRIES, LTD., Tokyo (JP)

( * ) Notice: Subject to any disclaimer, the term of this patent is extended or adjusted under 35 U.S.C. 154(b) by 148 days.

(21) Appl. No.: 15/028,239

(22) PCT Filed: Oct. 8, 2014

(86) PCT No.: PCT/JP2014/076959
§ 371 (c)(1),
(2) Date: Apr. 8, 2016

(87) PCT Pub. No.: WO2015/053320
PCT Pub. Date: Apr. 16, 2015

(65) Prior Publication Data
US 2016/0248018 A1    Aug. 25, 2016

(30) Foreign Application Priority Data

Oct. 9, 2013 (JP) .................. 2013-211829

(51) Int. Cl.
| | |
|---|---|
| *H01B 1/12* | (2006.01) |
| *H01L 51/00* | (2006.01) |
| *C07C 309/51* | (2006.01) |
| *H01L 51/50* | (2006.01) |
| *C07C 303/22* | (2006.01) |
| *C09D 5/24* | (2006.01) |

(52) U.S. Cl.
CPC ........ *H01L 51/0052* (2013.01); *C07C 303/22* (2013.01); *C07C 309/51* (2013.01); *C09D 5/24* (2013.01); *H01L 51/5088* (2013.01); *H01B 1/12* (2013.01); *H01L 51/0003* (2013.01); *H01L 2251/308* (2013.01)

(58) Field of Classification Search
CPC ....................................................... H01B 1/12
See application file for complete search history.

(56) References Cited

U.S. PATENT DOCUMENTS

| | | | | |
|---|---|---|---|---|
| 2,844,574 | A | * | 7/1958 | Gaspar et al. .......... C09B 39/00 430/519 |
| 2006/0115652 | A1 | | 6/2006 | Yoshimoto et al. |
| 2007/0105030 | A1 | | 5/2007 | Yoshimoto et al. |
| 2008/0029742 | A1 | | 2/2008 | Yoshimoto et al. |
| 2009/0058269 | A1 | * | 3/2009 | Ono ................. C08G 73/024 313/504 |
| 2010/0159279 | A1 | | 6/2010 | Kato et al. |
| 2010/0230639 | A1 | | 9/2010 | Yamada et al. |
| 2010/0320422 | A1 | | 12/2010 | Nakane et al. |

FOREIGN PATENT DOCUMENTS

| | | |
|---|---|---|
| CN | 101223254 A | 7/2008 |
| WO | WO 94/13277 A2 | 6/1994 |
| WO | WO 2004/043117 A1 | 5/2004 |
| WO | WO 2005/000832 A1 | 1/2005 |
| WO | WO 2006/025342 A1 | 3/2006 |
| WO | WO 2008/032616 A1 | 3/2008 |
| WO | WO 2008/129947 A1 | 10/2008 |
| WO | WO 2009/096352 A1 | 8/2009 |
| WO | WO 2010/058777 A1 | 5/2010 |

OTHER PUBLICATIONS

Office Action dated Jan. 22, 2017, in Chinese Patent Application No. 201480055509.4.
International Search Report (PCT/ISA/210) issued in PCT/JP2014/076959, dated Jan. 6, 2015.
Written Opinion (PCT/ISA/237) issued in PCT/JP2014/076959, dated Jan. 6, 2015.

* cited by examiner

*Primary Examiner* — William D Young
(74) *Attorney, Agent, or Firm* — Birch, Stewart, Kolasch & Birch, LLP

(57) ABSTRACT

Provided is an arylsulfonic acid compound characterized by being represented by formula (1).

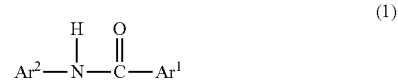

(1)

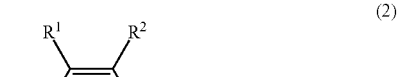

(2)

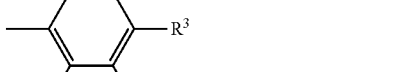

(3)

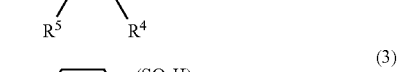

(4)

[In the formula, $Ar^1$ represents a group represented by formula (2) (in formula (2), $R^1$ to $R^5$ each independently represent a hydrogen atom, halogen atom, cyano group, nitro group, methyl group, or trifluoromethyl group; however, at least one of $R^1$ to $R^5$ represents a halogen atom) and $Ar^2$ represents a group represented by formula (3) or (4).]

12 Claims, No Drawings

ARYLSULFONIC ACID COMPOUND, USE THEREOF, AND METHOD FOR PRODUCING ARYLSULFONIC ACID COMPOUND

TECHNICAL FIELD

The invention relates to an arylsulfonic acid compound, its use, and a method for producing an arylsulfonic acid compound.

BACKGROUND ART

Organic electroluminescent (hereinafter referred to as "organic EL") devices make use of a charge transport thin film composed of an organic compound as a light emission layer or charge injection layer. Especially, a hole injection layer has a role of charge transport between an anode and a hole transport layer or light emission layer and plays an important function so as to achieve the low-voltage drive and high luminance of organic EL devices.

The formation of a hole injection layer is broadly classified into a dry process, typical of which is a vacuum deposition process, and a wet process, typical of which is a spin coating process. When comparing these processes with each other, a thin film having a large area and a high flatness can be formed more efficiently in the wet process. Therefore, a hole injection layer capable of being formed by the wet process has been demanded under the present situation where the formation of large-area organic EL displays is being in progress.

Under such circumstances, the inventors have developed charge transport materials that are applicable to a variety of wet processes and can be formed into a thin film capable of realizing excellent EL characteristics when applied to a hole injection layer of an organic EL device, and also compounds that are soluble in organic solvents used for the charge transport material and are useful as a charge transport material or dopant (e.g. see Patent Documents 1 to 7).

PRIOR ART DOCUMENTS

Patent Documents

Patent Document 1: WO 2008/032616
Patent Document 2: WO 2008/129947
Patent Document 3: WO 2006/025342
Patent Document 4: WO 2010/058777
Patent Document 5: WO 2005/000832
Patent Document 6: WO 2006/025342
Patent Document 7: WO 2009/096352

SUMMARY OF THE INVENTION

Problems to be Solved by the Invention

The invention has for its object the provision of an arylsulfonic acid compound which shows good solubility in organic solvents and can realize the formation of a thin film having excellent charge transportability when used along with charge transport materials as with the technologies of the above-indicated Patent Documents developed up to now and also a production method thereof.

Means for Solving the Problems

The inventors have made intensive studies so as to achieve the above object and, as a result, have found that the above object can be achieved by an arylsulfonic acid compound indicated below and that the arylsulfonic acid compound can be produced inexpensively and efficiently by a method indicated below, thereby arriving at completion of the invention.

More particularly, the invention provides the following arylsulfonic acid compound and its use, and a method for producing the arylsulfonic acid compound.

1. An arylsulfonic acid compound, characterized by being represented by formula (1):

[Chemical Formula 1]

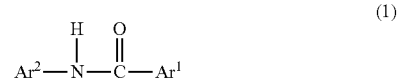

[wherein $Ar^1$ represents a group represented by formula (2):

[Chemical Formula 2]

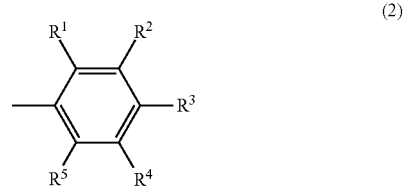

(wherein $R^1$ to $R^5$ independently represent a hydrogen atom, a halogen atom, a cyano group, a nitro group, a methyl group, or a trifluoromethyl group, provided that at least one of $R^1$ to $R^5$ represents a halogen atom), and $Ar^2$ represents a group represented by formula (3) or (4):

[Chemical Formula 3]

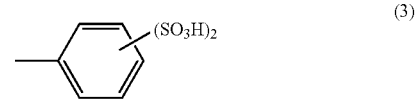

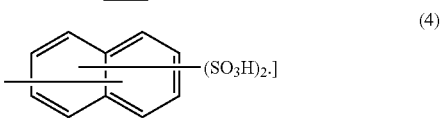

2. The arylsulfonic acid compound of 1, wherein $Ar^2$ represents a group represented by any one of formulas (3-1) and (3-2) and formulas (4-1) to (4-6):

[Chemical Formula 4]

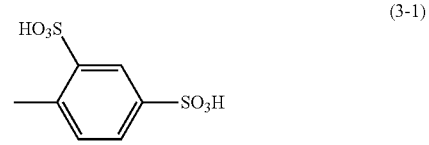

-continued (3-2) 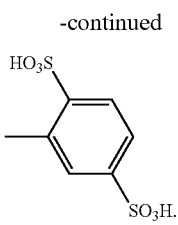

[Chemical Formula 5]

(4-1) 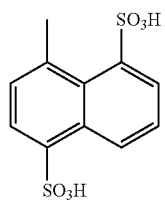

(4-2) 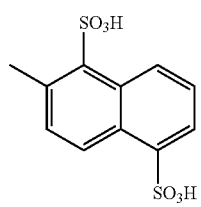

(4-3) 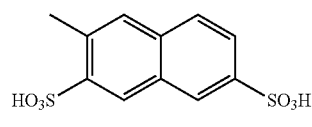

(4-4) 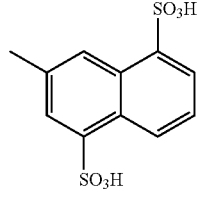

(4-5) 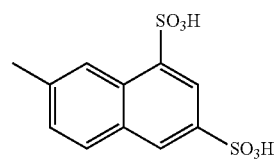

(4-6)

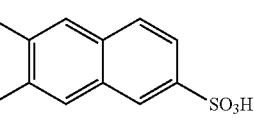

3. The arylsulfonic acid compound of 1 or 2, characterized in that at least one of $R^1$ to $R^5$ is a fluorine atom, and at least another one thereof is a halogen atom, a nitro group, a cyano group or a trifluoromethyl group.

4. A dopant composed of the arylsulfonic acid compound of any one of 1 to 3.

5. A charge transport varnish including the dopant of 4, a charge transport material and an organic solvent.

6. A charge transport thin film formed by use of the charge transport varnish of 5.

7. An organic electroluminescent device including the charge transport thin film of 6.

8. A method for producing a charge transport thin film, characterized by using the dopant of 4.

9. A method for producing a charge transport thin film, characterized by using the charge transport varnish of 5.

10. An arylsulfonic acid salt, characterized by being represented by formula (1'):

[Chemical Formula 6]

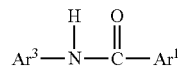

(1')

[wherein $Ar^1$ represents a group represented by formula (2):

[Chemical Formula 7]

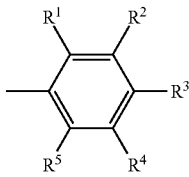

(2)

(wherein $R^1$ to $R^5$ independently represent a hydrogen atom, a halogen atom, a cyano group, a nitro group, a methyl group, or a trifluoromethyl group provided that at least one of $R^1$ to $R^5$ represents a halogen atom), and $Ar^3$ represents a group represented by formula (3') or (4'):

[Chemical Formula 8]

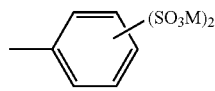

(3')

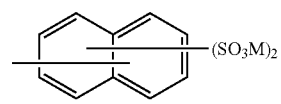

(4')

(wherein M represents an alkali metal atom)].

11. A method for producing the arylsulfonic acid salt of 10, characterized by reacting an amine represented by formula (5) with an acid halide compound represented by formula (6):

[Chemical Formula 9]

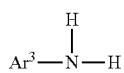

(5)

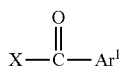

(6)

(wherein X represents a halogen atom, and $Ar^1$ and $Ar^3$ have the same meanings as defined above).

12. A method for producing the arylsulfonic acid compound of 1, characterized in that an arylsulfonic acid salt represented by formula (1') is subjected to ion exchange treatment:

[Chemical Formula 10]

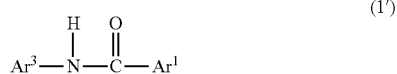
(1')

[wherein $Ar^1$ has the same meaning as defined above, and $Ar^3$ represents a group represented by formula (3') or (4'):

[Chemical Formula 11]

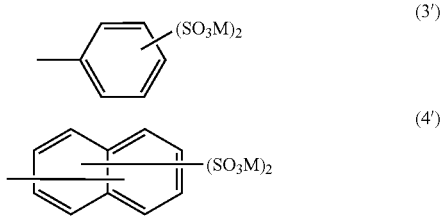

(wherein M represents an alkali metal atom)].

Advantageous Effects of the Invention

The arylsulfonic acid compound of the invention exhibits good solubility in organic solvents and can provide a thin film of excellent charge transportability when used along with a charge transport material.

According to the method for producing an arylsulfonic acid compound of the invention, the arylsulfonic acid compound can be produced inexpensively and efficiently.

EMBODIMENT FOR CARRYING OUT THE INVENTION

[Arylsulfonic Acid Compound]

The arylsulfonic acid compound of the invention is represented by formula (1):

[Chemical Formula 12]

(1)

$Ar^1$ represents a group represented by formula (2):

[Chemical Formula 13]

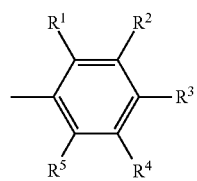
(2)

$R^1$ to $R^5$ independently represent a hydrogen atom, a halogen atom, a cyano group, a nitro group, a methyl group, or a trifluoromethyl group, provided that at least one of $R^1$ to $R^5$ represents a halogen atom.

The halogen atom includes fluorine atom, chlorine atom, bromine atom, or iodine atom, of which fluorine atom is preferred.

Especially, from the standpoint of obtaining a thin film having higher charge transportability when used together with a charge transport material, it is preferred that at least one of $R^1$ to $R^5$ is a fluorine atom and at least another one thereof is a group having good electron-withdrawing properties.

More particularly, it is preferred that at least one of $R^1$ to $R^5$ is a fluorine atom, and at least another one thereof is a halogen atom, a nitro group, a cyano group, or a trifluoromethyl group. More preferably, at least one of $R^1$ to $R^5$ is a fluorine atom, and at least another one thereof is a fluorine atom, a cyano group, a nitro group, or a trifluoromethyl group. Much more preferably, at least another one is a fluorine atom, a cyano group, or a nitro group, and most preferably, at least two of $R^1$ to $R^5$ are fluorine atoms.

Preferred examples of the group represented by formula (2) are those indicated below, but are not limited thereto.

[Chemical Formula 14]

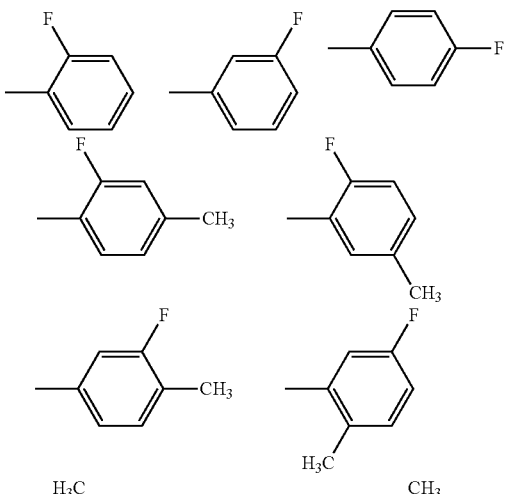

[Chemical Formula 15]

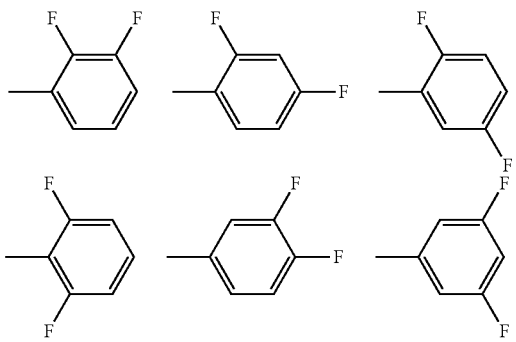

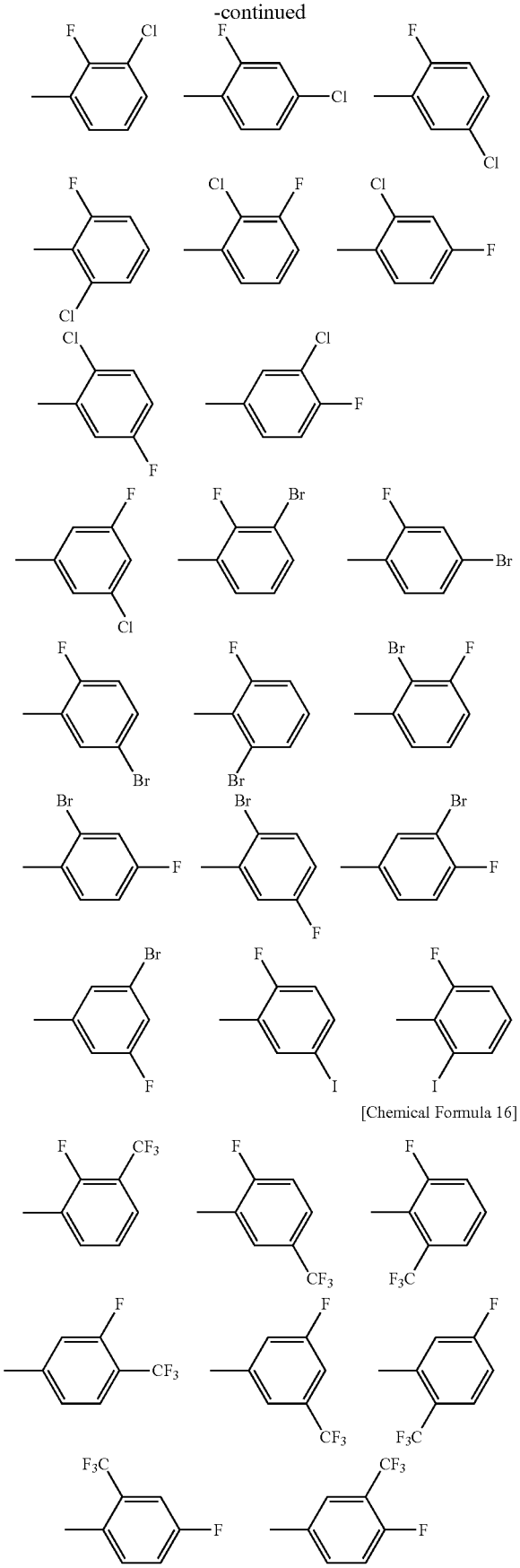
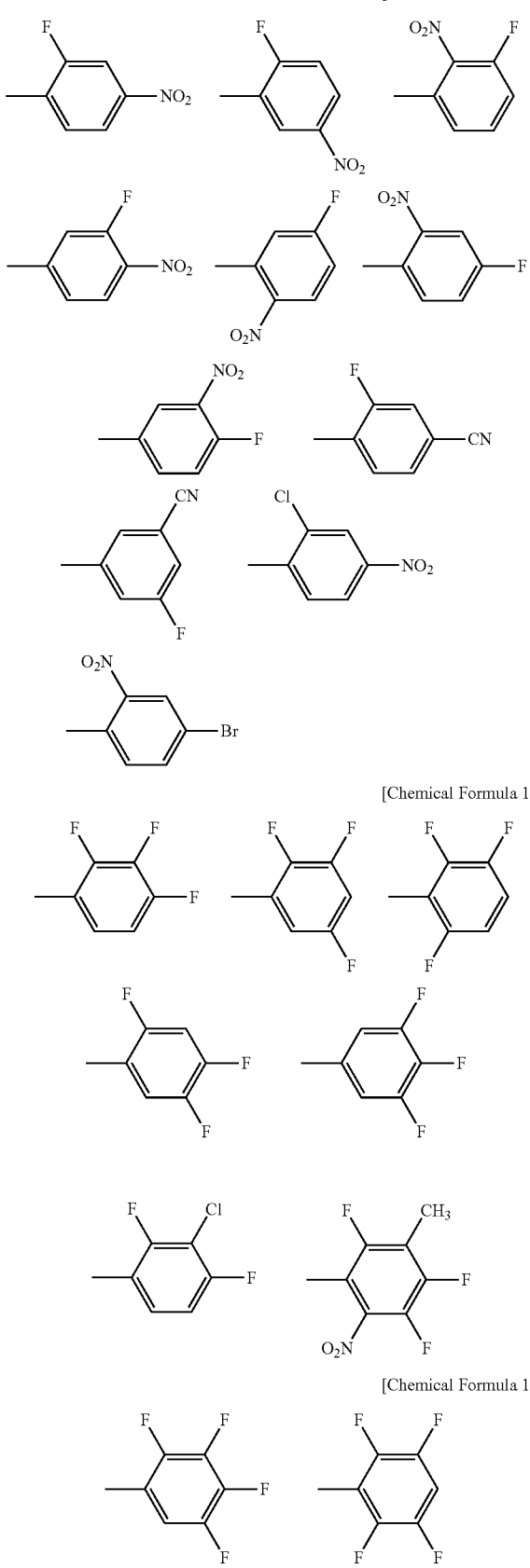

-continued

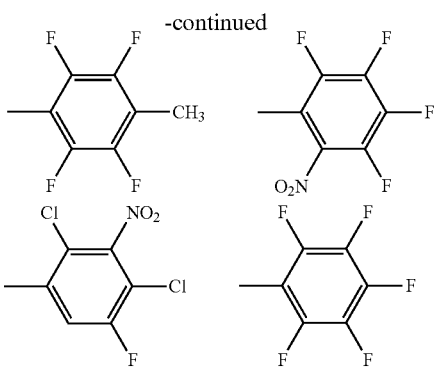

In formula (1), $Ar^2$ represents a group represented by formula (3) or (4):

[Chemical Formula 20]

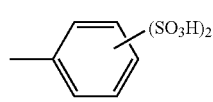
(3)

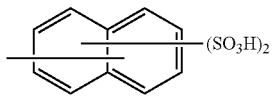
(4)

$Ar^2$ is preferably a group represented by formula (4) in view of the point that when used along with a charge transport material, a charge transport thin film of higher durability is obtained.

Preferred $Ar^2$ is a group represented, for example, by formula (4"):

[Chemical Formula 21]

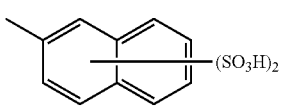
(4")

From the standpoint of ease in availability of starting compounds, the group represented by formula (3) preferably includes ones indicated below, but is not limited thereto:

[Chemical Formula 22]

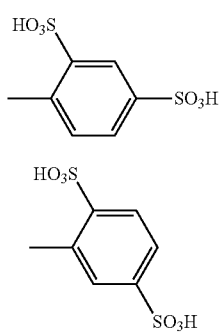

(3-1)

(3-2)

From the standpoint of ease in availability of starting compounds, the group represented by formula (4) preferably includes ones indicated below, but is not limited thereto:

[Chemical Formula 23]

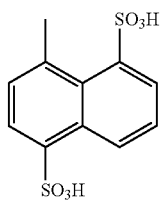
(4-1)

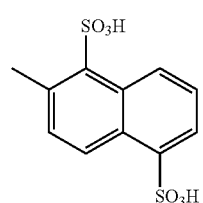
(4-2)

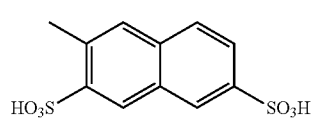
(4-3)

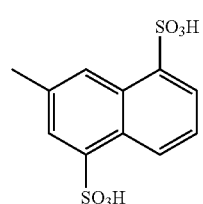
(4-4)

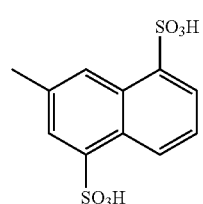
(4-5)

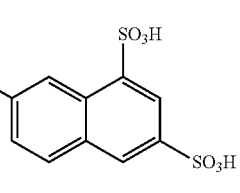
(4-6)

[Method of Producing an Arylsulfonic Acid Compound]

The arylsulfonic acid compound of the invention represented by formula (1) can be obtained by reacting an amine compound represented by formula (5) with an acid halide represented by formula (6) to obtain an arylsulfonic acid salt represented by formula (1') and subjecting the salt to ion exchange treatment:

[Chemical Formula 24]

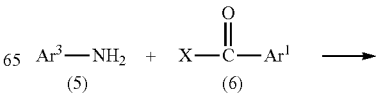

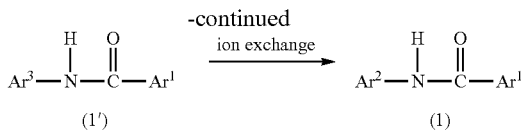

[wherein X represents a halogen atom, $Ar^1$ and $Ar^2$ have the same meanings as defined above, and $Ar^3$ represents a group represented by formula (3') or (4'):

[Chemical Formula 25]

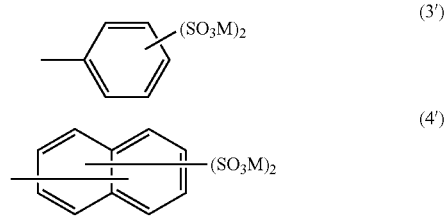

(wherein M represents an alkali metal atom such as sodium or potassium)].

The amine compound represented by formula (5) includes disodium aniline-2,4-disulfonate, disodium aniline-2,5-disulfonate, disodium 8-aminonaphthalene-1,5-disulfonate, disodium 2-aminonaphthalene-1,5-disulfonate, disodium 2-aminonaphthalene-3,6-disulfonate, disodium 7-aminonaphthalene-1,5-disulfonate, disodium 7-aminonaphthalene-2,4-disulfonate, or disodium 7-aminonaphthalene-1,3-disulfonate, but is not limited thereto. It is to be noted that the amine compound represented by formula (5) may be a hydride thereof.

The acid halide represented by formula (6) includes 2-fluorobenzoyl chloride, 3-fluorobenzoyl chloride, 4-fluorobenzoyl chloride, 2-fluoro-4-methylbenzoyl chloride, 2-fluoro-5-methylbenzoyl chloride, 3-fluoro-4-methylbenzoyl chloride, 3-fluoro-6-methylbenzoyl chloride, 4-fluoro-2-methylbenzoyl chloride, 4-fluoro-3-methylbenzoyl chloride, 2,3-difluorobenzoyl chloride, 2,4-difluorobenzoyl chloride, 2,5-difluorobenzoyl chloride, 2,6-difluorobenzoyl chloride, 3,4-difluorobenzoyl chloride, 3,5-difluorobenzoyl chloride, 3-chloro-2-fluorobenzoyl chloride, 4-chloro-2-fluorobenzoyl chloride, 5-chloro-2-fluorobenzoyl chloride, 2-chloro-6-fluorobenzoyl chloride, 2-chloro-3-fluorobenzoyl chloride, 2-chloro-4-fluorobenzoyl chloride, 2-chloro-5-fluorobenzoyl chloride, 3-chloro-4-fluorobenzoyl chloride, 3-chloro-5-fluorobenzoyl chloride, 3-bromo-2-fluorobenzoyl chloride, 4-bromo-2-fluorobenzoyl chloride, 5-bromo-2-fluorobenzoyl chloride, 2-bromo-6-fluorobenzoyl chloride, 2-bromo-3-fluorobenzoyl chloride, 2-bromo-4-fluorobenzoyl chloride, 2-bromo-5-fluorobenzoyl chloride, 3-bromo-4-fluorobenzoyl chloride, 3-bromo-5-fluorobenzoyl chloride, 2-fluoro-5-iodobenzoyl chloride, 2-fluoro-6-iodobenzoyl chloride, 2-fluoro-3-trifluoromethylbenzoyl chloride, 2-fluoro-5-trifluoromethylbenzoyl chloride, 2-fluoro-6-trifluoromethylbenzoyl chloride, 3-fluoro-4-trifluoromethylbenzoyl chloride, 3-fluoro-5-trifluoromethylbenzoyl chloride, 3-fluoro-6-trifluoromethylbenzoyl chloride, 4-fluoro-2-trifluoromethylbenzoyl chloride, 4-fluoro-3-trifluoromethylbenzoyl chloride, 2-fluoro-4-nitrobenzoyl chloride, 2-fluoro-5-nitrobenzoyl chloride, 3-fluoro-2-nitrobenzoyl chloride, 3-fluoro-4-nitrobenzoyl chloride, 3-fluoro-6-nitrobenzoyl chloride, 4-fluoro-2-nitrobenzoyl chloride, 4-fluoro-3-nitrobenzoyl chloride, 4-cyano-2-fluorobenzoyl chloride, 3-cyano-5-fluorobenzoyl chloride, 2-chloro-4-nitrobenzoyl chloride, 4-bromo-2-nitrobenzoyl chloride, 2,3,4-trifluorobenzoyl chloride, 2,3,5-trifluorobenzoyl chloride, 2,3,6-trifluorobenzoyl chloride, 2,4,5-trifluorobenzoyl chloride, 3,4,5-trifluorobenzoyl chloride, 4-chloro-2,4-difluorobenzoyl chloride, 2,4-dichloro-5-fluoro-4-nitrobenzoyl chloride, 2,4,5-trifluoro-3-methyl-6-nitrobenzoyl chloride, 2,3,4,5-tetrafluorobenzoyl chloride, 2,3,5,6-tetrafluorobenzoyl chloride, 2,3,5,6-tetrafluoro-4-methylbenzoyl chloride, 2,3,4,5-tetrafluoro-6-nitrobenzoyl chloride, or 2,3,4,5,6-pentafluorobenzoyl chloride, but is not limited thereto.

The reaction solvent is preferably an aprotic polar organic solvent. Examples include N,N-dimethylformamide, N,N-dimethylacetamide, N-methylpyrrolidone, 1,3-dimethyl-2-imidazolidinone, dimethylsulfoxide, tetrahydrofuran, and dioxane. From the standpoint of ease in removal of the reaction solvent after reaction, N,N-dimethylformamide, N,N-dimethylacetamide, tetrahydrofuran, dioxane and the like are preferred.

The reaction temperature is generally from −50° C. to a boiling point of a solvent used and is preferably within a range of 0 to 140° C. The reaction time is generally from 0.1 to 100 hours.

After completion of the reaction, the arylsulfonic acid salt represented by formula (1') is collected by filtration, removal by distillation of the reaction solvent, or the like. Thereafter, the sulfonic acid salt is protonated with a cation exchange resin, for example, to produce the arylsulfonic acid compound represented by formula (1).

The acid halide represented by formula (6) can be obtained by reacting a corresponding carboxylic acid with an electrophilic halogenating agent such, for example, as thionyl chloride, oxalyl chloride, phosphoryl chloride, sulfuryl chloride, phosphorus trichloride, or phosphorus pentachloride.

[Charge Transport Varnish]

The charge transport varnish of the invention contains the above arylsulfonic acid compound as a dopant, along with a charge transport material and an organic solvent.

The charge transport material contained in the charge transport varnish of the invention is a material having charge transportability, or conductivity, and may be one that has charge transportability in itself or may be one that exhibits charge transportability when used with a dopant. Especially, materials having hole transportability are preferred.

Usable charge transport materials include ones hitherto employed in the field of organic EL or the like. Specific examples include a variety of charge transport compounds: arylamine derivatives (or aniline derivatives) such as oligoaniline derivatives, N,N'-diarylbenzidine derivatives and N,N,N',N'-tetraarylbenzidine derivatives; thiophene derivatives such as oligothiophene derivatives, thienothiophene derivatives and thienobenzothiophene derivatives; and pyrrole derivatives such as oligopyrrole. Of these, arylamine derivatives and thiophene derivatives are preferred.

In the invention, the molecular weight of the charge transport compound is generally at about 200 to 9,000 from the standpoint of preparing a uniform varnish capable of forming a highly flat thin film. In view of the point of obtaining a thin film having more excellent charge transportability, the molecular weight is preferably at least 300, more preferably at least 400. From the standpoint of preparing a uniform varnish capable of forming a highly flat thin film more reproducibly, the molecular weight is preferably up to 8,000, more preferably up to 7,000, much more preferably up to 6,000 and most preferably up to 5,000. In view of the point of preventing the charge transport material from separating when thinned, the charge transport compound has preferably no molecular weight distribution (i.e. dispersivity=1) (that is, the material preferably has a single molecular weight).

Preferred examples of the charge transport material include oligoaniline derivatives indicated in JP 2002-151272 A, oligoaniline compounds indicated in WO 2004/105446, compounds with a 1,4-dithiin ring indicated in WO 2005/043962, oligoaniline compounds indicated in WO 2008/032617, oligoaniline compounds indicated in WO 2008/032616, and aryldiamine compounds indicated in WO 2013/042623, but are not limited thereto.

Specific examples of the arylamine derivatives are indicated below, but are not limited thereto.

[Chemical Formula 26]

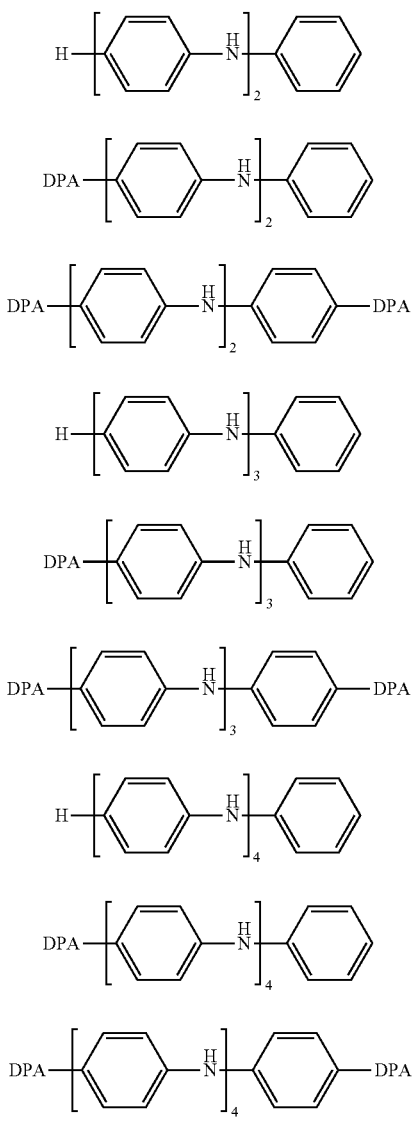

(wherein DPA represents a diphenylamino group.)

[Chemical Formula 27]

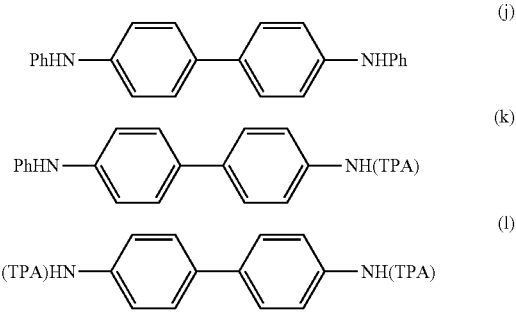

(wherein Ph represents a phenyl group, and TPA represents a p-(diphenylamino)phenyl group.)

Specific examples of the thiophene derivatives are indicated below, but are not limited thereto.

[Chemical Formula 28]

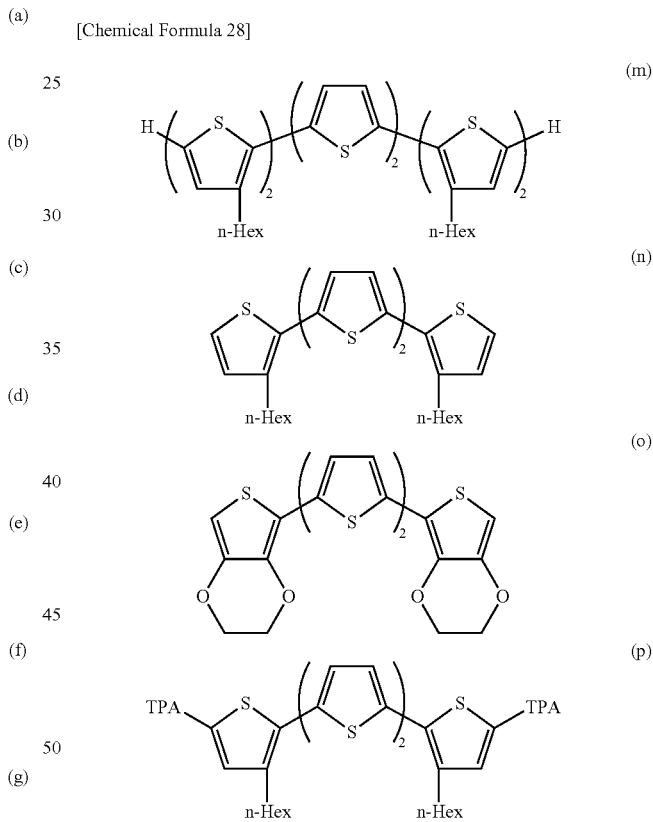

(wherein n-Hex represents an n-hexyl group, and TPA represents a p-(diphenylamino)phenyl group.)

Although the ratio of the charge transport material and the arylsulfonic acid compound in the charge transport varnish of the invention is not specifically limited, the arylsulfonic acid compound should preferably be at 0.25 to 5 equivalents, more preferably at 0.5 to 2 equivalents, relative to the charge transport material when considering improved characteristics of organic EL, devices provided with the resulting charge transport thin film.

The organic solvent used for the preparation of the charge transport varnish can be a high solubility solvent capable of well dissolving a charge transport material and a dopant.

Such a high solubility solvent includes an organic solvent such as N,N-dimethylformamide, N,N-dimethylacetamide, N-methylpyrrolidone, 1,3-dimethyl-2-imidazolidinone, and diethylene glycol monomethyl ether. These solvents may be used singly or in combination of at least two. The amount may be set at 5 to 100 wt % relative to the total solvent used in the varnish.

It is preferred that the charge transport material and dopant are both completely dissolved in solvents.

In the invention, when at least one high viscosity organic solvent having a viscosity of 10 to 200 mPa·s, preferably 35 to 150 mPa·s, at 25° C. and a boiling point of 50 to 300° C., preferably 150 to 250° C. at a normal pressure (atmospheric pressure) is contained in the varnish, the viscosity of the varnish can be easily adjusted. As a consequence, it becomes possible to prepare a varnish that is capable of reproducibly providing a highly flat thin film and is appropriate for the manner of coating used.

The high viscosity organic solvent is not specifically limited and includes, for example, cyclohexanol, ethylene glycol, ethylene glycol diglycidyl ether, 1,3-octylene glycol, diethylene glycol, dipropylene glycol, triethylene glycol, tripropylene glycol, 1,3-butanediol, 2,3-butanediol, 1,4-butanediol, propylene glycol, and hexylene glycol. These solvents may be used singly or in combination of at least two.

The ratio of the high viscosity organic solvent to the total solvent in the varnish of the invention is preferably within, a range not permitting solids to precipitate, and is preferably at 5 to 80 wt % in so far as solids do not precipitate.

Further, in order to improve wettability to a substrate and adjust the surface tension, polarity and boiling point of a solvent, other type of solvent may be mixed at a ratio to the total solvent used in the varnish of 1 to 90 wt %, preferably 1 to 50 wt %.

Examples of such a solvent include ethylene glycol monobutyl ether, diethylene glycol diethyl ether, diethylene glycol dimethyl ether, diethylene glycol monoethyl ether acetate, diethylene glycol monobutyl ether acetate, dipropylene glycol monomethyl ether, propylene glycol monomethyl ether acetate, diethylene glycol monoethyl ether, diacetone alcohol, γ-butyrolactone, ethyl lactate, n-hexyl acetate, and propylene glycol monomethyl ether, but are not limited thereto. These solvents may be used singly or in admixture of at least two.

Although the viscosity of the varnish of the invention should be appropriately set depending on the thickness of a produced thin film and the solid concentration, it is generally 1 to 50 mPa·s at 25° C.

The solid concentration of the charge transport varnish of the invention should be appropriately set while considering the viscosity and surface tension of the varnish and the thickness of a produced thin film and is generally about 0.1 to 10.0 wt %. When considering the improved coatability of the varnish, the solid concentration is preferably about 0.5 to 5.0 wt %, more preferably about 1.0 to 3.0 wt %.

In the invention, from the standpoint of reproducibly obtaining a highly flat thin film it is preferred that the charge transport varnish is filtrated with a filter on the order of sub-micrometers after dissolution of a charge transport material, a dopant and the like in organic solvents.

[Charge Transport Thin Film]

When the charge transport varnish of the invention is coated onto a substrate and baked, a charge transport thin film can be formed on the substrate.

The coating method of the varnish includes a dipping method, a spin coating method, a transfer printing method, a roll coating method, a brushing method, an ink jet method, or a spraying method, but is not limited thereto. The viscosity and surface tension of the varnish should be preferably adjusted depending on the coating method.

To obtain a thin film having a uniform film surface and high charge transportability in the case where the varnish of the invention is used, a baking environment (under atmospheric conditions, in an inert gas such as nitrogen, or in vacuum) needs to be selected while taking the types of charge transport material and solvent contained in the varnish along with the arylsulfonic acid of the invention into consideration. In most cases, baking in an air atmosphere enables a uniform thin film having excellent charge transportability to be obtained.

The baking temperature is appropriately set within a range of about 100 to 260° C. while considering the use of an obtained thin film, the degree of charge transportability to be imparted to the obtained thin film, and the like. In the case where the resulting thin film is used as a hole injection layer of an organic EL device, the temperature is preferably about 140 to 250° C., more preferably about 145° C. to 240° C.

For the purposes of developing more uniform film formability and causing the reaction to proceed on a substrate during baking, the temperature may be changed in at least two stages. Heating may be carried out by using, for example, an appropriate device such as a hot plate or an oven.

The thickness of the charge transport thin film is not specifically limited. With the case of using the film as a hole injection layer in an organic EL device, the thickness is preferably 5 to 200 nm. The film thickness may be changed by changing a solid concentration in the varnish or by changing an amount of a coating solution on a substrate.

[Organic EL Device]

The organic EL device of the invention has a pair of electrodes, and the charge transport thin film of the invention formed between these electrodes.

Typical configurations of the organic EL device include those indicated as (a) to (f) below, but are not limited thereto. It is to be noted that in the following configurations, an electron blocking layer or the like may be provided between a light-emitting layer and an anode, and a hole blocking layer may be provided between a light-emitting layer and a cathode, if necessary. Moreover, a hole injection layer, a hole transport layer or a hole injection and transport layer may also have a function as an electron blocking layer. Additionally, an electron injection layer, an electron transport layer or an electron injection and transport layer may also have a function as a hole blocking layer.

(a) Anode/hole injection layer/hole transport layer/light-emitting layer/electron transport layer/electron injection layer/cathode (b) Anode/hole injection layer/hole transport layer/light-emitting layer/electron injection and transport layer/cathode (c) Anode/hole injection and transport layer/light-emitting layer/electron transport layer/electron injection layer/cathode (d) Anode/hole injection and transport layer/light-emitting layer/electron injection and transport layer/cathode (e) Anode/hole injection layer/hole transport layer/light-emitting layer/cathode (f) Anode/hole injection and transport layer/light-emitting layer/cathode The "hole injection layer," "hole transport layer" and "hole injection and transport layer" are each a layer formed between a light-emitting layer and an anode and have a function of transporting holes from the anode to the light-emitting layer. The case where only one layer of a hole transport material is formed between the light-emitting layer and the anode means "hole injection and transport layer." In the case where at least two layers of a hole transport material are formed between the light-emitting layer and the anode, a layer closer to the anode is "hole injection layer" and the other layers are "hole transport layers." Especially, the hole injection layer (or the hole injection and transport layer) used should be formed of a thin film which is excellent not only in hole acceptability from the anode, but also in hole injectability into the hole transport layer (or the light-emitting layer).

The "electron injection layer," "electron transport layer" and "electron injection and transport layer" are each a layer formed between a light-emitting layer and a cathode and have a function of transporting electrons from the cathode to the light-emitting layer. The case where only one layer of an electron transport material is formed between the light-emitting layer and the cathode means "electron injection and transport layer." In the case where at least two layers of an electron transport material are formed between the light-emitting layer and the cathode, a layer closer to the cathode is "electron injection layer" and the other layers are "electron transport layers."

The "light-emitting layer" means an organic layer having a light-emitting function, and if a doping system is adopted, the layer contains a host material and a dopant material. On this occasion, the host material has a function of mainly promoting the recombination of electrons and holes and confining the resulting excitons within the light-emitting layer, and the dopant material has a function of permitting efficient light emission of the excitons obtained by the recombination. With a phosphorescent device, the host material has a function of mainly confining the excitons generated on a dopant within the light-emitting layer.

The charge transport thin film of the invention can be conveniently used as a hole injection layer, a hole transport layer or a hole injection and transport layer in organic EL devices and can be more conveniently used as a hole injection layer.

Where organic EL devices are fabricated using the charge transport varnish of the invention, the materials used and fabrication methods may be those set out below, but are not limited thereto.

The electrode substrate used should preferably be cleaned beforehand by washing with liquids such as a detergent, alcohol or pure water. For example, with an anode substrate, it is preferred to perform a surface treatment, such as a UV ozone treatment or an oxygen-plasma treatment, immediately before use. In this regard, however, where the anode material is composed mainly of an organic matter, it may be possible not to carry out the surface treatment.

An instance of a fabrication method of an organic EL device having a hole injection layer formed of a thin film obtained from the charge transport varnish of the invention is described below.

The charge transport varnish of the invention is coated onto an anode substrate and baked according to the method stated above to form a hole injection layer on the electrode. The hole injection layer is formed thereon with a hole transport layer, a light-emitting layer, an electron transport layer, an electron injection layer and a cathode in this order. The hole transport layer, light-emitting layer, electron transport layer and electron injection layer can be formed by either of a vacuum deposition method or a coating method (wet process) depending on the characteristics of the material used.

The anode materials include transparent electrodes, typical of which are indium tin oxide (ITO) and indium zinc oxide (IZO), and metal anodes constituted of metals such as aluminum and alloys thereof. Planarized anodes are preferred. Polythiophene derivatives and polyaniline derivatives having high charge transportability may also be used.

Other types of metals constituting the metal anode include scandium, titanium, vanadium, chromium, manganese, iron, cobalt, nickel, copper, zinc, gallium, yttrium, zirconium, niobium, molybdenum, ruthenium, rhodium, palladium, cadmium, indium, scandium, lanthanum, cerium, praseodymium, neodymium, promethium, samarium, europium, gadolinium, terbium, dysprosium, holmium, erbium, thulium, ytterbium, hafnium, thallium, tungsten, rhenium, osmium, iridium, platinum, gold, titanium, lead, bismuth, and alloys thereof, but are not limited thereto.

The materials for forming the hole transport layer include hole transport low molecular weight materials such as (triphenylamine)dimer derivatives, [(triphenylamine)dimer] spiro dimer, N,N'-bis(naphthalen-1-yl)-N,N'-bis(phenyl)-benzidine (α-NPD), N,N'-bis(naphthalen-2-yl)-N,N'-bis(phenyl)-benzidine, N,N'-bis(3-methylphenyl)-N,N'-bis(phenyl)-benzidine, N,N'-bis(3-methylphenyl)-N,N'-bis(phenyl)-9,9-spirofluorene, N,N'-bis(naphthalen-1-yl)-N,N'-bis(phenyl)-9,9-spirofluorene, N,N'-bis(3-methylphenyl)-N,N'-bis(phenyl)-9,9-dimethylfluorene, N,N'-bis(naphthalen-1-yl)-N,N'-bis(phenyl)-9,9-dimethylfluorene, N,N'-bis(3-methylphenyl)-N,N'-bis(phenyl)-9,9-diphenyl-fluorene, N,N'-bis(naphthalen-1-yl)-N,N'-bis(phenyl)-9,9-diphenyl-fluorene, N,N'-bis(naphthalen-1-yl)-N,N'-bis(phenyl)-2,2'-dimethylbenzidine, 2,2',7,7'-tetrakis(N,N-diphenylamino)-9,9-spirobifluorene, 9,9-bis[4-(N,N-bis-biphenyl-4-yl-amino)phenyl]-9H-fluorene, 9,9-bis[4-(N,N-bis-naphthalen-2-yl-amino)phenyl]-9H-fluorene, 9,9-bis[4-(N-naphthalen-1-yl-N-phenylamino)-phenyl]-9H-fluorene, 2,2',7,7'-tetrakis[N-naphthalenyl(phenyl)-amino]-9,9-spirobifluorene, N,N'-bis(phenanthren-9-yl)-N,N'-bis(phenyl)-benzidine, 2,2'-bis[N,N-bis(biphenyl-4-yl)amino]-9,9-spirobifluorene, 2,2'-bis(N,N-diphenylamino)-9,9-spirobifluorene, di-[4-(N,N-di(p-tolyl)amino)-phenyl]cyclohexane, 2,2',7,7'-tetra(N,N-di(p-tolyl)amino)-9,9-spirobifluorene, N,N,N',N'-tetra-naphthalen-2-yl-benzidine, N,N,N',N'-tetra-(3-methylphenyl)-3,3'-dimethylbenzidine, N,N'-di(naphthalenyl)-N,N'-di(naphthalen-2-yl)-benzidine, N,N,N',N'-tetra(naphthalenyl)-benzidine, N,N'-di(naphthalen-2-yl)-N,N'-diphenylbenzidine-1,4-diamine, $N^1,N^4$-diphenyl-$N^1$,$N^4$-di(m-tolyl)benzene-1,4-diamine, $N^2,N^2,N^6,N^6$-tetraphenylnaphthalene-2,6-diamine, tris(4-(quinolin-8-yl)phenyl)amine, 2,2'-bis(3-(N,N-di(p-tolyl)amino)phenyl)biphenyl, triarylamines such as 4,4',4''-tris[3-methylphenyl(phenyl)amino]triphenylamine (m-MTDATA) and 4,4',4''-tris[1-naphthyl(phenyl)amino]triphenylamine (1-TNATA), and oligothiophenes such as 5,5''-bis-{4-[bis(4-methylphenyl)amino]phenyl}-2,2':5',2''-terthiophene (BMA-3T).

The materials for forming the light-emitting layer include tris(8-quinolinolato)aluminum(III) ($Alq_3$), bis(8-quinolinolato)zinc(II) ($Znq_2$), bis(2-methyl-8-quinolinolato)-4-(p-phenylphenolato)-aluminum(III) (BAlq), 4,4'-bis(2,2-diphenylvinyl)biphenyl, 9,10-di(naphthalen-2-yl)anthracene, 2-t-butyl-9,10-di(naphthalen-2-yl)anthracene, 2,7-bis[9,9-di(4-methylphenyl)-fluoren-2-yl]-9,9-di(4-methylphenyl) fluorene, 2-methyl-9,10-bis(naphthalen-2-yl)anthracene, 2-(9,9-spirobifluoren-2-yl)-9,9-spirobifluorene, 2,7-bis(9,9-spirobifluoren-2-yl)-9,9-spirobifluorene, 2-[9,9-di(4-methylphenyl)-fluoren-2-yl]-9,9-di(4-methylphenyl)fluorene, 2,2'-dipyrenyl-9,9-spirobifluorene, 1,3,5-tris(pyren-1-yl)benzene, 9,9-bis[4-(pyrenyl)phenyl]-9H-fluorene, 2,2'-bi(9, 10-diphenylanthracene), 2,7-dipyrenyl-9,9-spirobifluorene, 1,4-di(pyren-1-yl)benzene, 1,3-di(pyren-1-yl)benzene, 6,13-di(biphenyl-4-yl)pentacene, 3,9-di(naphthalen-2-yl)perylene, 3,10-di(naphthalen-2-yl)perylene, tris[4-(pyrenyl)-phenyl]amine, 10,10'-di(biphenyl-4-yl)-9,9'-bianthracene, N,N'-di(naphthalen-1-yl)-N,N'-diphenyl-[1,1':4',1'':4'',1'''quaterphenyl]-4,4'''-diamine, 4,4'-di[10-(naphthalen-1-yl)anthracen-9-yl]biphenyl, dibenzo{[f,f']-4,4',7,7'-tetraphenyl}diindino[1,2,3-cd:1',2',3'-lm]perylene, 1-(7-(9,9'-bianthracen-10-yl)-9,9-dimethyl-9H-fluoren-2-yl)pyrene, 1-(7-(9,9'-bianthracen-10-yl)-9,9-dihexyl-9H-fluoren-2-yl)pyrene, 1,3-bis(carbazol-9-yl)benzene, 1,3,5-tris(carbazol-9-yl)benzene, 4,4',4''-tris(carbazol-9-yl)triphenylamine, 4,4'-bis(carbazol-9-yl)biphenyl (CBP), 4,4'-bis(carbazol-9-yl)-2,2'-dimethylbiphenyl, 2,7-bis(carbazol-9-yl)-9,9-dimethylfluorene, 2,2',7,7'-tetrakis(carbazol-9-yl)-9,9-spirobifluorene, 2,7-bis(carbazol-9-yl)-9,9-di(p-tolyl)fluorene, 9,9-bis[4-(carbazol-9-yl)-phenyl]fluorene, 2,7-bis(carbazol-9-yl)-9,9-spirobifluorene, 1,4-bis(triphenylsilyl)benzene, 1,3-bis(triphenylsilyl)benzene, bis(4-N,N-diethylamino-2-methylphenyl)-4-methylphenylmethane, 2,7-bis(carbazol-9-yl)-9,9-dioctylfluorene, 4,4''-di(triphenylsilyl)-p-terphenyl, 4,4'-di(triphenylsilyl)biphenyl, 9-(4-t-butylphenyl)-3,6-bis(triphenylsilyl)-9H-carbazole, 9-(4-t-butylphenyl)-3,6-ditrityl-9H-carbazole, 9-(4-t-butylphenyl)-3,6-bis(9-(4-methoxyphenyl)-9H-fluoren-9-yl)-9H-carbazole, 2,6-bis(3-(9H-carbazol-9-yl)phenyl)pyridine, triphenyl(4-(9-phenyl-9H-fluoren-9-yl)phenyl)silane, 9,9-dimethyl-N,N-diphenyl-7-(4-(1-phenyl-1H-benz[d]imidazol-2-yl)phenyl)-9H-fluorene-2-amine, 3,5-bis(3-(9H-carbazol-9-yl)phenyl)pyridine, 9,9-spirobifluoren-2-yl-diphenyl-phosphine oxide, 9,9'-(5-(triphenylsilyl)-1,3-phenylene)bis(9H-carbazole), 3-(2,7-bis(diphenylphosphoryl)-9-phenyl-9H-fluoren-9-yl)-9-phenyl-9H-carbazole, 4,4,8,8,12,12-hexa(p-tolyl)-4H-8H-12H-12C-azadibenzo-[cd,mn]pyrene, 4,7-di(9H-carbazol-9-yl)-1,10-phenanthroline, 2,2'-bis(4-(carbazol-9-yl)phenyl)biphenyl, 2,8-bis(diphenylphosphoryl)dibenzo[b,d]thiophene, bis(2-methylphenyl)diphenylsilane, bis[3,5-di(9H-carbazol-9-yl)phenyl]diphenylsilane, 3,6-bis(carbazol-9-yl)-9-(2-ethyl-hexyl)-9H-carbazole, 3-(diphenylphosphoryl)-9-(4-(diphenylphosphoryl)phenyl)-9H-carbazole, and 3,6-bis[(3,5-diphenyl)phenyl]-9-phenylcarbazole.

A light-emitting layer may be formed by co-deposition with a light-emitting dopant.

Examples of the light-emitting dopant include 3-(2-benzothiazolyl)-7-(diethylamino)coumarin, 2,3,6,7-tetrahydro-1,1,7,7-tetramethyl-1H,5H,11H-10-(2-benzothiazolyl)quinolizino[9,9a,1gh]coumarin, quinacridone, N,N'-dimethylquinacridone, tris(2-phenylpyridine)iridium(III) (Ir(ppy)$_3$), bis(2-phenylpyridine)(acetylacetonate)iridium(III) (Ir(ppy)$_2$(acac)), tris[2-(p-tolyl)pyridine]iridium(III) (Ir(mppy)$_3$), 9,10-bis[N,N-di(p-tolyl)amino]anthracene, 9,10-bis[phenyl(m-tolyl)amino]anthracene, bis[2-(2-hydroxyphenyl)benzothiazolato]zinc(II), $N^{10},N^{10},N^{10},N^{10}$-tetra(p-tolyl)-9,9'-bianthracene-10,10'-diamine, $N^{10},N^{10},N^{10},N^{10}$-tetraphenyl-9,9'-bianthracene-10,10'-diamine, $N^{10},N^{10}$-diphenyl-$N^{10}$,$N^{10}$-dinaphthalenyl-9,9'-bianthracene-10,10'-diamine, 4,4'-bis(9-ethyl-3-carbazovinylene)-1,1'-biphenyl, perylene, 2,5,8,11-tetra-t-butylperylene, 1,4-bis[2-(3-N-ethylcarbazolyl)vinyl]benzene, 4,4'-bis[4-(di-p-tolylamino)styryl]biphenyl, 4-(di-p-tolylamino)-4'-[(di-p-tolylamino)styryl]stylbene, bis[3,5-difluoro-2-(2-pyridyl)phenyl-(2-carboxypyridyl)]-iridium(III), 4,4'-bis[4-(diphenylamino)styryl]biphenyl, bis(2,4-difluorophenylpyridinato)tetrakis(1-pyrazolyl)borate iridium(III), N,N'-bis(naphthalen-2-yl)-N,N'-bis(phenyl)-tris(9,9-dimethylfluorenylene), 2,7-bis{2-[phenyl(m-tolyl)amino]-9,9-dimethyl-fluoren-7-yl}-9,9-dimethylfluorene, N-(4-((E)-2-(6((E)-4-(diphenylamino)styryl)naphthalen-2-yl)vinyl)phenyl)-N-phenylbenzeneamine, fac-iridium(III)tris(1-phenyl-3-methylbenzimidazolin-2-ylidene-C,C$^2$), mer-iridium(III)tris(1-phenyl-3-methylbenzimidazolin-2-ylidene-C,C$^2$), 2,7-bis[4-(diphenylamino)styryl]-9,9-spirofluorene, 6-methyl-2-(4-(9-(4-(6-methylbenzo[d]thiazol-2-yl)phenyl)anthracen-10-yl)phenyl)benzo[d]thiazole, 1,4-di[4-(N,N-diphenyl)amino]styrylbenzene, 1,4-bis(4-(9H-carbazol-9-yl)styryl)benzene, (E)-6-(4-(diphenylamino)styryl)-N,N-diphenylnaphthalene-2-amine, bis(2,4-difluorophenylpyridinato)(5-(pyridin-2-yl)-1H-tetrazolato)iridium(III), bis(3-trifluoromethyl-5-(2-pyridyl)pyrazole)((2,4-difluorobenzyl)diphenylphosphinate)iridium(III), bis(3-trifluoromethyl-5-(2-pyridyl)pyrazolate)(benzyl-diphenylphosphinate)iridium(III), bis(1-(2,4-difluorobenzyl)-3-methylbenzimidazolium)(3-(trifluoromethyl)-5-(2-pyridyl)-1,2,4-triazolate)iridium(III), bis(3-trifluoromethyl-5-(2-pyridyl)pyrazolate)(4',6'-difluorophenylpyridinate)iridium(III), bis(4',6'-difluorophenylpyridinato)(3,5-bis(trifluoromethyl)-2-(2'-pyridyl)pyrolate)iridium(III), bis(4',6'-difluorophenylpyridinato)(3-(trifluoromethyl)-5-(2-pyridyl)-1,2,4-triazolate)iridium(III), (Z)-6-mesityl-N-(6-mesitylquinoline-2(1H)-ylidene)quinoline-2-amine-BF$_2$, (E)-2-(2-(4-(dimethylamino)styryl)-6-methyl-4H-pyran-4-ylidene)malononitrile, 4-(dicyanomethylene)-2-methyl-6-julolidyl-9-enyl-4H-pyrane, 4-(dicyanomethylene)-2-methyl-6-(1,1,7,7-tetramethyl-julolidyl-9-enyl)-4H-pyrane, 4-(dicyanomethylene)-2-t-butyl-6-(1,1,7,7-tetramethyl-julolidin-4-yl-vinyl)-4H-pyrane, tris(dibenzoylmethane)phenanthroline europium(III), 5,6,11,12-tetraphenylnaphthacene, bis(2-benzo[b]thiophen-2-yl-pyridine)(acetylacetonate)-iridium(III), tris(1-phenylisoquinoline)iridium(III), bis(1-phenylisoquinoline)(acetylacetonate)iridium(III), bis[1-(9,9-dimethyl-9H-fluoren-2-yl)-isoquinoline](acetyl-acetonate)iridium(III), bis[2-(9,9-dimethyl-9H-fluoren-2-yl)quinoline](acetyl-acetonate)iridium(III), tris[4,4'-di-t-butyl-(2,2')-bipyridine]ruthenium(III).bis(hexafluorophosphate), tris(2-phenylquinoline)iridium(III), bis(2-phenylquinoline)(acetylacetonate)iridium(III), 2,8-di-t-butyl-5,11-bis(4-t-butylphenyl)-6,12-diphenyltetracene, bis(2-phenylbenzothiazolato)(acetylacetonate)iridium(III), 5,10,15,20-tetraphenyltetrabenzoporphyrin platinum, osmium(II)bis(3-trifluoromethyl-5-(2-pyridine)-pyrazolate) dimethylphenylphospine, osmium(II)bis(3-(trifluoromethyl)-5-(4-t-butylpyridyl)-1,2,4-triazolate) diphenylmethylphosphine, osmium(II)bis(3-(trifluoromethyl)-5-(2-pyridyl)-1,2,4-triazole) dimethylphenylphosphine, osmium(II)bis(3-(trifluoromethyl)-5-(4-t-butylpyridyl)-1,2,4-triazolate) dimethylphenylphosphine, bis[2-(4-n-hexylphenyl)quinoline](acetylacetonate)iridium(III), tris[2-(4-n-hexylphenyl)quinoline]iridium(III), tris[2-phenyl-4-methylquinoline]iridium(III), bis(2-phenylquinoline)(2-(3-methylphenyl)pyridinate)-iridium(III), bis(2-(9,9-diethyl-fluoren-2-yl)-1-phenyl-1H-benzo[d]imidazolato) (acetylacetonate)iridium(III), bis(2-phenylpyridine)(3-(pyridin-2-yl)-2H-chromen-2-onate)-iridium(III), bis(2-phenylquinoline)(2,2,6,6-tetramethylheptan-3,5-dionate) iridium(III), bis(phenylisoquinoline)(2,2,6,6-tetramethylheptan-3,5-dionate)iridium(III), iridium(III)bis(4-phenylthieno[3,2-c]pyridinato-N,C$^2$)acetylacetonate, (E)-2-(2-t-butyl-6-(2-(2,6,6-trimethyl-2,4,5,6-tetrahydro-1H-pyrrolo[3,2,1-ij]quinolin-8-yl)vinyl)-4H-pyran-4-ylidene)-malononitrile, bis(3-trifluoromethyl-5-(1-isoquinolyl)pyrazolate)(methyl-diphenylphosphine)ruthenium, bis

[(4-n-hexylphenyl)isoquinoline](acetylacetonate)-iridium(III), platinum(II)octaethylporphine, bis(2-methyldibenzo[f,h]quinoxaline)(acetylacetonate)-iridium(III), and tris[(4-n-hexylphenyl)isoquinoline]iridium(III).

The materials for forming the electron transport layer include 8-hydroxyquinolinolate-lithium, 2,2',2"-(1,3,5-benzinetolyl)-tris(1-phenyl-1-H-benzimidazole), 2-(4-biphenyl)5-(4-t-butylphenyl)-1,3,4-oxadiazole, 2,9-dimethyl-4,7-diphenyl-1,10-phenanthroline, 4,7-diphenyl-1,10-phenanthroline, bis(2-methyl-8-quinolinolate)-4-(phenylphenolato)aluminum, 1,3-bis[2-(2,2'-bipyridin-6-yl)-1,3,4-oxadiazo-5-yl]benzene, 6,6'-bis[5-(biphenyl-4-yl)-1,3,4-oxadiazo-2-yl]-2,2'-bipyridine, 3-(4-biphenyl)-4-phenyl-5-t-butylphenyl-1,2,4-triazole, 4-(naphthalen-1-yl)-3,5-diphenyl-4H-1,2,4-triazole, 2,9-bis(naphthalen-2-yl)-4,7-diphenyl-1,10-phenanthroline, 2,7-bis[2-(2,2'-bipyridin-6-yl)-1,3,4-oxadiazo-5-yl]-9,9-dimethylfluorene, 1,3-bis[2-(4-t-butylphenyl)-1,3,4-oxadiazo-5-yl]benzene, tris(2,4,6-trimethyl-3-(pyridin-3-yl)phenyl)borane, 1-methyl-2-(4-(naphthalen-2-yl)phenyl)-1H-imidazo-[4,5f][1,10]phenanthroline, 2-(naphthalen-2-yl)-4,7-diphenyl-1,10-phenanthroline, phenyl-dipyrenylphosphine oxide, 3,3',5,5'-tetra[(m-pyridyl)-phen-3-yl]biphenyl, 1,3,5-tris[(3-pyridyl)-phen-3-yl]benzene, 4,4'-bis(4,6-diphenyl-1,3,5-triazin-2-yl)biphenyl, 1,3-bis[3,5-di(pyridin-3-yl)phenyl]benzene, bis(10-hydroxybenzo[h]quinolinato]beryllium, diphenylbis(4-(pyridin-3-yl)phenyl)silane, and 3,5-di(pyren-1-yl)pyridine.

The materials for forming the electron injection layer include lithium oxide ($Li_2O$), magnesium oxide (MgO), alumina ($Al_2O_3$), lithium fluoride (LiF), sodium fluoride (NaF), magnesium fluoride ($MgF_2$), cesium fluoride (CsF), strontium fluoride ($SrF_2$), molybdenum trioxide ($MoO_3$), aluminum, Li(acac), lithium acetate, and lithium benzoate.

The cathode materials include aluminum, magnesium-silver alloy, aluminum-lithium alloy, lithium, sodium, potassium, and cesium.

Other example of a method for fabricating an organic EL device having a hole injection layer formed of a thin film obtained from the charge transport varnish of the invention is as described below.

In the fabrication of the EL device, when a hole transport layer (hereinafter referred to as hole transport polymer layer) and a light-emitting layer (hereinafter referred to as light-emitting polymer layer) are successively formed in place of the vacuum deposition operations of a hole transport layer, a light-emitting layer, an electron transport layer and an electron injection layer, there can be fabricated an organic EL device having a charge transport thin film formed from the charge transport varnish of the invention. More particularly, the charge transport varnish of the invention is coated onto an anode substrate to form a hole injection layer by the above method, on which a hole transport polymer layer and a light-emitting polymer layer are successively formed, followed by vacuum deposition of a cathode electrode to provide an organic EL device.

The cathode and anode materials used may be those indicated above and can be subjected to similar washing and surface treatments.

Examples of the formation method of the hole transport polymer layer and the light-emitting polymer layer include a method wherein a hole transport polymer material or a light-emitting polymer material with or without addition of a dopant material is dissolved or uniformly dispersed in a solvent, followed by coating onto a hole injection layer or a hole transport polymer layer and baking to form a film.

The hole transport polymer materials include poly[(9,9-dihexylfluorenyl-2,7-diyl)-co-(N,N'-bis{p-butylphenyl}-1,4-diaminophenylene)], poly[(9,9-dioctylfluorenyl-2,7-diyl)-co-(N,N'-bis{p-butylphenyl}-1,1'-biphenylene-4,4-diamine)], poly[(9,9-bis{1'-penten-5'-yl}fluorenyl-2,7-diyl)-co-(N,N'-bis{p-butylphenyl}-1,4-diaminophenylene)], poly[N,N'-bis(4-butylphenyl)-N,N'-bis(phenyl)-benzidine]-end-capped with polysilsesquioxane, and poly[(9,9-dioctylfluorenyl-2,7-diyl)-co-(4,4'-(N-(p-butylphenyl))diphenylamine)].

The light-emitting polymer materials include polyfluorene derivatives such as poly(9,9-dialkylfluorene) (PDAF), polyphenylenevinylene derivatives such as poly(2-methoxy-5-(2'-ethylhexoxy)-1,4-phenylenevinylene) (MEH-PPV), polythiophene derivatives such as poly(3-alkylthiophene) (PAT), and polyvinylcarbazole (PVCz).

The solvents include toluene, xylene, and chloroform. The dissolution or uniform dispersion methods include those methods of agitation, agitation under heating, and ultrasonic dispersion.

The coating method is not specifically limited and includes, for example, an ink jet method, a spraying method, a dipping method, a spin coating method, a transfer printing method, a roll coating method, and a brushing method. It is to be noted that the coating is preferably carried out in an inert gas such as of nitrogen or argon.

The baking method may be a method of heating in an oven or with a hot plate in an inert gas or in vacuum.

An example of a method for fabricating an organic EL device having a hole transport layer formed of a thin film obtained from the charge transport varnish of the invention is as described below.

A hole injection layer is formed on an anode substrate. The charge transport varnish of the invention is coated on the hole injection layer by the method described above and baked to form a hole transport layer. A light-emitting layer, an electron transport layer, an electron injection layer and a cathode are formed on the hole transport layer in this order. The manner of forming the light-emitting layer, electron transport layer and electron injection layer and specific examples therefor are those set out hereinabove. The hole injection layer may be formed by either of a vacuum deposition method or a coating (wet process) method depending on the characteristic properties of materials used.

The materials for forming the hole injection layer include copper phthalocyanine, titanium oxide phthalocyanine, platinum phthalocyanine, pyrazino[2,3-f][1,10]phenanthroline-2,3-dicarbonitrile, N,N,N',N'-tetrakis(4-methoxyphenyl)benzidine, 2,7-bis[N,N-bis(4-methoxy-phenyl)amino]-9,9-spirobifluorene, 2,2'-bis[N,N-bis(4-methoxy-phenyl)amino]-9,9-spirobifluorene, N,N'-diphenyl-N,N'-di[4-(N,N-ditolylamino)phenyl]benzidine, N,N'-diphenyl-N,N'-di[4-(N,N-diphenylamino)phenyl]benzidine, $N^4,N^{4'}$-(biphenyl-4,4'-diyl)bis($N^4,N^{4'},N^{4'}$-triphenylbiphenyl-4,4'-diamine)$N^1$, $N^{1'}$-(biphenyl-4,4'-diyl)bis($N^1$-phenyl-$N^4,N^{4'}$-di-m-tolylbenzene-1,4-diamine), and those charge transport materials indicated in WO Nos. 2004/043117, 2004/105446, 2005/000832, 2005/043962, 2005/042621, 2005/107335, 2006/006459, 2006/025342, 2006/137473, 2007/049631, 2007/099808, 2008/010474, 2008/032617, 2008/032616, 2008/129947, 2009/096352, 2010/041701, 2010/058777, 2010/058776, 2013/042623, 2013/129249, 2014/115865, 2014/132917, 2014/141998, and 2014/132834.

The anode materials, materials for forming the light-emitting layer, light-emitting dopant, electron transport layer and electron blocking layer, and cathode materials are those as indicated above.

An example of the method for fabricating an organic EL device having a hole injection and transport layer formed of a thin film obtained from the charge transport varnish of the invention is as described below.

A hole injection and transport layer is formed on an anode substrate, and a light-emitting layer, an electron transport layer, an electron injection layer and a cathode are formed on the hole injection and transport layer in this order. The formation methods and specific examples of the light-emitting layer, electron transport layer and electron injection layer are similar to those set out above.

The anode materials, materials for forming the light-emitting layer, light-emitting dopant, electron transport layer and electron blocking layer, and cathode materials are those as indicated above.

It is to be noted that a hole blocking layer, an electron blocking layer and the like may be optionally provided between arbitrary adjacent layers of the electrodes and the respective layers, if necessary. For example, materials for forming the electron blocking layer include tris(phenylpyrazole)iridium.

The types of materials of the anode, the cathode and the layer formed therebetween differ depending on whether the device to be fabricated is designed to have a top emission structure or a bottom emission structure, and are thus appropriately selected with the above in view.

In general, with a device of a bottom emission structure, a transparent anode is used at the substrate side to take out light from the substrate side, whereas with a device of a top emission structure, a reflective anode composed of metal is used and light is taken out from a transparent electrode (cathode) located opposite to the substrate. With respect to an anode material, for example, a transparent anode such as ITO is used for the fabrication of a device of a bottom emission structure and a reflective anode such as Al/Nd is used for the fabrication of a device of a top emission structure.

The organic EL device of the invention may be encapsulated along with a moisture catcher so as to prevent characteristic deterioration as usual, if necessary.

EXAMPLES

The invention is more particularly illustrated by way of Examples, which should not be construed as limiting the invention thereto. $^1$H-NMR measurement was carried out using a high resolution nuclear magnetic resonance spectrometer, manufactured by Varian Inc.

[1] Synthesis of Compounds

Example 1

Synthesis of Arylsulfonic Acid Compound 1

[Chemical Formula 29]

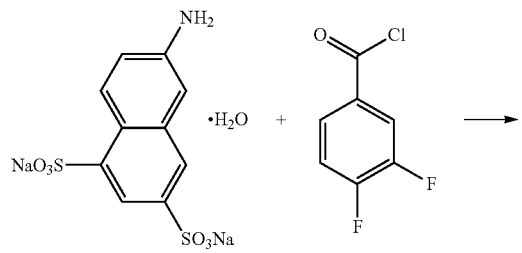

-continued

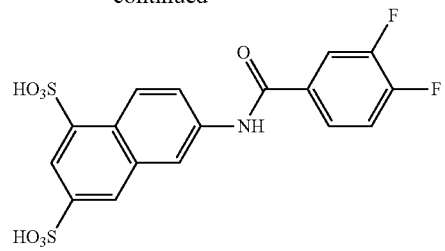

5.43 g of 3,4-difluorobenzoic acid chloride (manufactured by Tokyo Chemical Industry Co., Ltd.) was put in a 100 mL flask, followed by purging with nitrogen and further adding 80 g of N,N-dimethylacetamide. The resulting mixture was agitated under heating at 50° C. for 10 minutes. 10.0 g of disodium 6-amino-1,3-naphthalenedisulfonate hydrate (manufactured by Tokyo Chemical Industry Co., Ltd.) was added to the mixture and agitated at 50° C. for further 15 minutes, followed by allowing the reaction mixture to cool.

Next, the solvent was distilled off from the thus cooled reaction mixture under reduced pressure, and the resulting residue and 20 mL of methanol were mixed and filtered. While keeping 400 mL of a mixed solvent of isopropanol and n-hexane (isopropanol/n-hexane=3/1 (v/v)) under agitation, the filtrate obtained above was slowly dropped into the mixed solvent, followed by further agitation for 30 minutes.

After completion of the agitation, the resulting suspension was filtered and the solvent was removed from the filtrate under reduced pressure. The resulting residue was dissolved in 50 mL of a mixed solvent of water and methanol (water/methanol=1/1 (v/v)). The resulting solution was used to perform column chromatography with cation exchange resin Dowex 650C (about 200 mL of H type, distillate solvent: water/methanol=1/1 (v/v)).

Finally, the solvent was distilled off under reduced pressure and the resulting solid was well dried under reduced pressure to obtain intended arylsulfonic acid compound 1 (yield: 12.5 g). The results of the $^1$H-NMR measurement were indicated below.

$^1$H-NMR (400 MHz, DMSO-d6) δ [ppm]: 8.77 (d, J=9.2 Hz, 1H), 8.39 (d, J=2.4 Hz, 1H), 8.15 (d, J=1.6 Hz, 1H), 8.10 to 8.13 (m, 1H), 7.99 to 8.00 (s, 1H), 7.93 to 7.97 (m, 1H), 7.85 (dd, J=9.2, 2.4 Hz, 1H), and 7.62 to 7.69 (m, 1H).

Example 2

Synthesis of Arylsulfonic Acid Compound 2

[Chemical Formula 30]

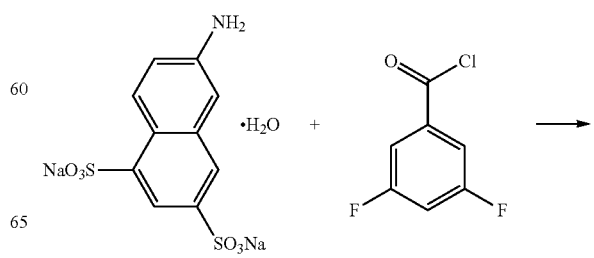

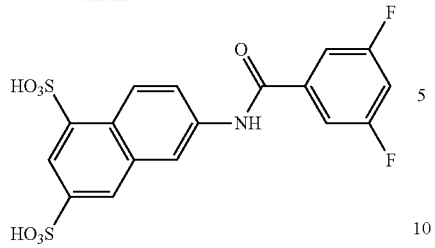

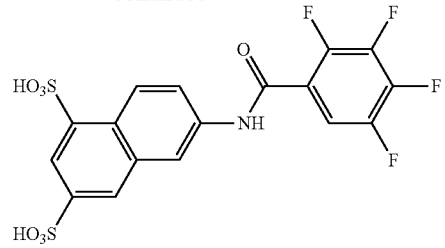

5.43 g of 3,5-difluorobenzoic acid chloride (manufactured by Tokyo Chemical Industry Co., Ltd.) was put in a 50 mL flask, followed by purging with nitrogen and further adding 80 g of N,N-dimethylacetamide thereto. The resulting mixture was agitated under heating at 50° C. for 10 minutes. 10.0 g of disodium 6-amino-1,3-naphthalenedisulfonate hydrate (manufactured by Tokyo Chemical Industry Co., Ltd.) was added to the mixture and agitated at 50° C. for further 15 minutes, followed by allowing the reaction mixture to cool.

Next, the solvent was distilled off from the thus cooled reaction mixture under reduced pressure, and the resulting residue and 20 mL of methanol were mixed and filtered. While keeping 300 mL of isopropanol under agitation, the filtrate obtained above was slowly dropped into the isopropanol, followed by further agitation for 30 minutes.

After completion of the agitation, the resulting suspension was filtered and the solvent was removed from the filtrate under reduced pressure. The resulting residue was dissolved in 50 mL of a mixed solvent of water and methanol (water/methanol=1/1 (v/v)). The resulting solution was used to perform column chromatography with cation exchange resin Dowex 650C (about 200 mL of H type, distillate solvent: water/methanol=1/1 (v/v)).

Finally, the solvent was distilled off under reduced pressure and the resulting solid was well dried under reduced pressure to obtain intended arylsulfonic acid compound 2 (yield: 6.2 g). The results of the $^1$H-NMR measurement were indicated below.

$^1$H-NMR (400 MHz, DMSO-d6) δ [ppm]: 10.60 (s, 1H), 8.77 (d, J=9.2 Hz, 1H), 8.40 (d, J=2.0 Hz, 1H), 8.15 (s, 1H), 7.99 (s, 1H), 7.84 (dd, J=9.2, 2.4 Hz, 1H), 7.78 to 7.75 (m, 2H), and 7.58 to 7.53 (m, 1H).

Example 3

Synthesis of Arylsulfonic Acid Compound 3

[Chemical Formula 31]

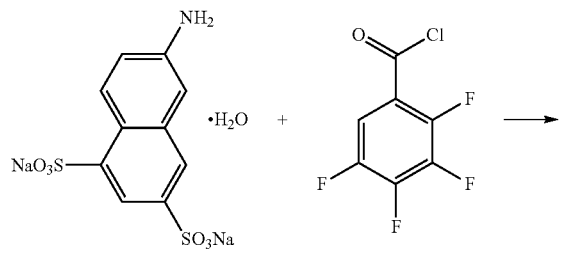

6.53 g of 2,3,4,5-tetrafluorobenzoic acid chloride (manufactured by Tokyo Chemical Industry Co., Ltd.) was put in a 100 mL flask, followed by purging with nitrogen and further adding 80 g of N,N-dimethylacetamide thereto. The resulting mixture was agitated under heating at 50° C. for 10 minutes. 10.0 g of disodium 6-amino-1,3-naphthalenedisulfonate hydrate (manufactured by Tokyo Chemical Industry Co., Ltd.) was added to the mixture and agitated at 50° C. for further 15 minutes, followed by allowing the reaction mixture to cool.

Next, the solvent was distilled off from the thus cooled reaction mixture under reduced pressure, and the resulting residue and 20 mL of methanol were mixed and filtered. While keeping 300 mL of isopropanol under agitation, the filtrate obtained above was slowly dropped into the isopropanol, followed by further agitation for 30 minutes.

After completion of the agitation, the resulting suspension was filtered and the solvent was removed from the filtrate under reduced pressure. The resulting residue was dissolved in 20 mL of water. The resulting solution was used to perform column chromatography with cation exchange resin Dowex 650C (about 200 mL of H type, distillate solvent: water).

Finally, the solvent was distilled off under reduced pressure and the resulting solid was well dried under reduced pressure to obtain intended arylsulfonic acid compound 3 (yield: 10 g). The results of the $^1$H-NMR measurement were indicated below.

$^1$H-NMR (400 MHz, DMSO-d6) δ [ppm]: 10.8 (s, 1H), 8.78 (d, J=9.2 Hz, 1H), 8.34 (d, J=2.0 Hz, 1H), 8.15 (d, J=1.6 Hz, 1H), 7.98 to 7.99 (m, 1H), 7.87 to 7.89 (m, 1H), and 7.73 (dd, J=9.2, 2.4 Hz, 1H).

[2] Preparation of Charge Transport Varnish

Example 4

0.077 g of an aniline derivative prepared according to the method described in Bulletin of Chemical Society of Japan, 1994, vol. 67, pp. 1749 to 1752 and represented by the following formula, and 0.163 g of arylsulfonic acid 1 were dissolved in 4 g of 1,3-dimethyl-2-imidazolidinone, to which 6 g of cyclohexanol and 2 g of propylene glycol were added and agitated. The resulting solution was filtered through a PTFE filter having a pore size of 0.2 μm to obtain charge transport varnish 1.

[Chemical Formula 32]

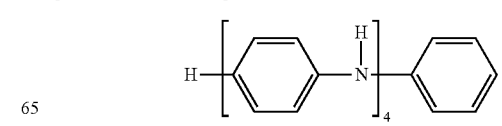

Example 5

Charge transport varnish 2 was obtained in the same manner as in Example 4 except that 0.168 g of arylsulfonic acid 3 was used in place of arylsulfonic acid 1.

[3] Fabrication of Device

Examples 6 and 7

The varnishes obtained in Examples 4 and 5 were each coated onto an ITO substrate by use of a spin coater and dried at 50° C. for 5 minutes, followed by baking in an air atmosphere at 230° C. for 15 minutes to form a 30 nm thick uniform thin film on the ITO substrate. The ITO substrate used was a 25 mm×25 mm×0.7 t glass substrate on which indium tin oxide (ITO) was patterned in a thickness of 150 nm. The impurities on the surface were removed prior to use by means of an $O_2$ plasma cleaner (150 W, 30 seconds).

Next, the thin films of N,N'-bis(naphthalen-1-yl)-N,N'-bis(phenyl)benzidine (α-NPD), tris(8-quinolilato)aluminum (III) ($Alq_3$), lithium fluoride and aluminum were successively stacked on the thin film-formed ITO substrate by use of a vacuum deposition device (degree of vacuum: $1.0 \times 10^{-5}$ Pa) to obtain an organic EL device. On this occasion, the deposition rates were at 0.2 nm/second for α-NPD, $Alq_3$ and aluminum and at 0.02 nm/second for lithium fluoride, and the respective film thicknesses were at 30 nm, 40 nm, 0.5 nm, and 120 nm.

To prevent characteristic deterioration by the influence of oxygen, moisture and the like in air, the organic EL device was encapsulated with sealing or encapsulating substrates and its characteristics were evaluated. The encapsulating was carried out according to the following procedure.

The organic EL device was placed between sealing or encapsulating substrates in a nitrogen atmosphere having an oxygen concentration of up to 2 ppm and a dew point of up to −85° C., and the sealing or encapsulating substrates were bonded with each other by an adhesive material (XNR5516Z-B1, manufactured by Nagase ChemteX Corporation). On this occasion, a moisture catcher (HD-071010W-40, manufactured by Dynic Corporation) had been placed in the sealing or encapsulating substrates along with the organic EL device.

The thus bonded sealing or encapsulating substrates were irradiated with UV light (wavelength: 365 nm, irradiation quantity: 6,000 mJ/cm²), followed by annealing at 80° C. for 1 hour to cure the adhesive material.

These devices were subjected to measurement of a luminance at a drive voltage of 5 V. The results are shown in Table 1.

TABLE 1

| | Varnish | Current density (mA/cm²) | Luminance (cd/m²) | Current efficiency (cd/A) |
|---|---|---|---|---|
| Example 6 | Charge transport varnish 1 | 175 | 4,458 | 2.6 |
| Example 7 | Charge transport varnish 2 | 186 | 4,859 | 2.6 |

As shown in Table 1, it was found out that when using a charge transport varnish including an arylsulfonic acid compound of the invention and a charge transport material, an organic EL device of high luminance can be realized and a charge transport thin film suited as a hole injection layer can be obtained.

The invention claimed is:

1. An arylsulfonic acid compound, characterized by being represented by formula (1):

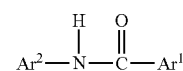

(1)

wherein $Ar^1$ represents a group represented by formula (2):

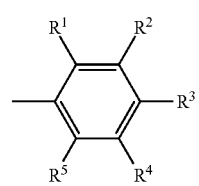

(2)

wherein $R^1$ to $R^5$ independently represent a hydrogen atom, a halogen atom, a cyano group, a nitro group, a methyl group, or a trifluoromethyl group, provided that at least one of $R^1$ to $R^5$ represents a halogen atom, and $Ar^2$ represents a group represented by formula (3) or (4):

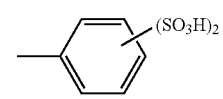

(3)

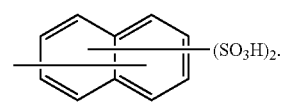

(4)

2. The arylsulfonic acid compound of claim 1, wherein $Ar^2$ represents a group represented by any one of formulas (3-1) and (3-2) and formulas (4-1) to (4-6):

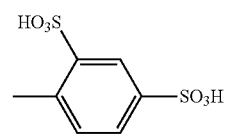

(3-1)

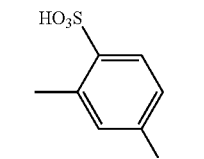

(3-2)

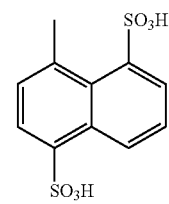

(4-1)

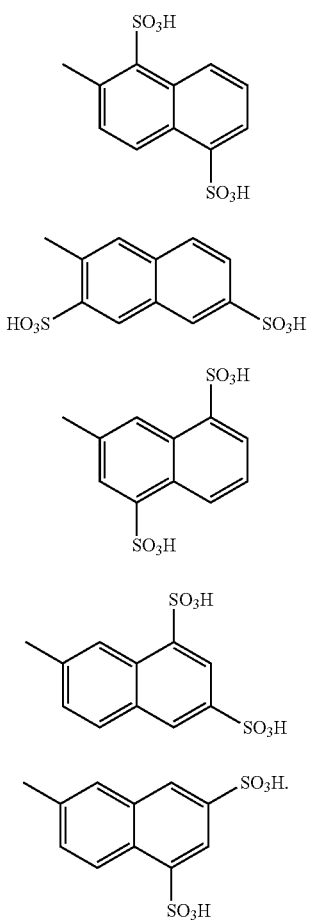

(4-2)

(4-3)

(4-4)

(4-5)

(4-6)

3. The arylsulfonic acid compound of claim 1 or 2, wherein at least one of $R^1$ to $R^5$ is a fluorine atom, and at least another one of $R^1$ to $R^5$ is a halogen atom, a nitro group, a cyano group or a trifluoromethyl group.

4. A dopant comprising the arylsulfonic acid compound of claim 1.

5. A charge transport varnish comprising the dopant of claim 4, a charge transport material, and an organic solvent.

6. A charge transport thin film obtained from baking the charge transport varnish of claim 5.

7. An organic electroluminescent device comprising the charge transport thin film of claim 6.

8. A method for producing a charge transport thin film, comprising the step of coating on a substrate and baking the charge transport varnish of claim 5.

9. An arylsulfonic acid salt, characterized by being represented by formula (1'):

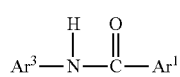

(1')

wherein $Ar^1$ represents a group represented by formula (2):

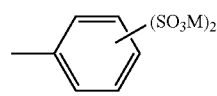

(2)

wherein $R^1$ to $R^5$ independently represent a hydrogen atom, a halogen atom, a cyano group, a nitro group, a methyl group, or a trifluoromethyl group provided that at least one of $R^1$ to $R^5$ represents a halogen atom, and $Ar^3$ represents a group represented by formula (3') or (4'):

[Chemical Formula 8]

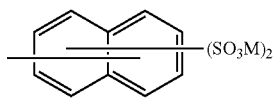

(3')

(4')

wherein M represents an alkali metal atom.

10. A method for producing the arylsulfonic acid salt of claim 9, comprising the step of reacting an amine represented by formula (5) with an acid halide compound represented by formula (6):

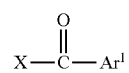

(5)

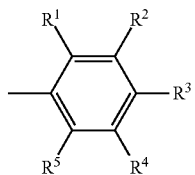

(6)

wherein X represents a halogen atom, and $Ar^1$ represents a group represented by formula (2):

(2)

wherein $R^1$ to $R^5$ independently represent a hydrogen atom, a halogen atom, a cyano group, a nitro group, a methyl group, or a trifluoromethyl group, provided that at least one of $R^1$ to $R^5$ represents a halogen atom, and $Ar^3$ represents a group represented by formula (3') or (4'):

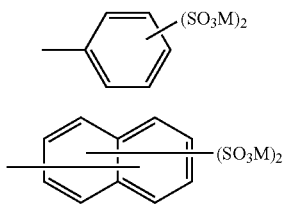

wherein M represents an alkali metal atom.

11. A method for producing the arylsulfonic acid compound of claim 1, comprising the step of ion-exchange treatment of an arylsulfonic acid salt represented by formula (1'):

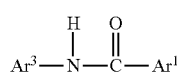

wherein Ar$^1$ represents a group represented by formula (2):

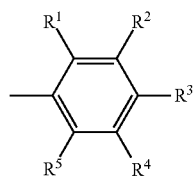

wherein R$^1$ to R$^5$ independently represent a hydrogen atom, a halogen atom, a cyano group, a nitro group, a methyl group, or a trifluoromethyl group, provided that at least one of R$^1$ to R$^5$ represents a halogen atom, and Ar$^3$ represents a group represented by formula (3') or (4'):

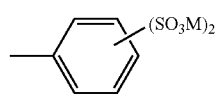

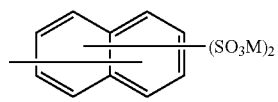

wherein M represents an alkali metal atom.

12. A charge transport thin film comprising a dopant and a charge transport material,
wherein the dopant comprises an arylsulfonic acid compound represented by formula (1):

wherein Ar$^1$ represents a group represented by formula (2):

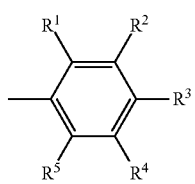

wherein R$^1$ to R$^5$ independently represent a hydrogen atom, a halogen atom, a cyano group, a nitro group, a methyl group, or a trifluoromethyl group, provided that at least one of R$^1$ to R$^5$ represents a halogen atom, and Ar$^2$ represents a group represented by formula (3) or (4):

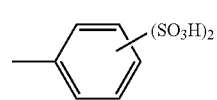

* * * * *